United States Patent
Bailey

(10) Patent No.: US 10,071,010 B2
(45) Date of Patent: Sep. 11, 2018

(54) METHOD AND APPARATUS FOR PERFORMING ON-SITE MOBILE DENTISTRY

(71) Applicant: Richard Bailey, Moscow, ID (US)

(72) Inventor: Richard Bailey, Moscow, ID (US)

(*) Notice: Subject to any disclaimer, the term of this patent is extended or adjusted under 35 U.S.C. 154(b) by 209 days.

(21) Appl. No.: 15/145,802

(22) Filed: May 4, 2016

(65) Prior Publication Data

US 2017/0319416 A1 Nov. 9, 2017

(51) Int. Cl.
| | |
|---|---|
| *A61G 15/00* | (2006.01) |
| *A61G 15/02* | (2006.01) |
| *A61G 15/12* | (2006.01) |
| *A61B 1/06* | (2006.01) |
| *A47C 7/72* | (2006.01) |

(52) U.S. Cl.
CPC ............ *A61G 15/002* (2013.01); *A47C 7/725* (2013.01); *A61B 1/06* (2013.01); *A61G 15/02* (2013.01); *A61G 15/125* (2013.01)

(58) Field of Classification Search
CPC .... A61G 15/002; A61G 15/02; A61G 15/125; A61B 1/06; A47C 7/725
USPC .......................................... 297/DIG. 4, 217.6
See application file for complete search history.

(56) References Cited

U.S. PATENT DOCUMENTS

| | | | | | |
|---|---|---|---|---|---|
| 1,469,928 | A | * | 10/1923 | Lazar ..................... | A61G 15/10 297/217.6 |
| 2,089,727 | A | * | 8/1937 | Borden ................... | A45D 44/04 132/229 |
| 4,242,086 | A | * | 12/1980 | Jorg ....................... | A61G 13/105 297/188.2 |
| 4,778,216 | A | * | 10/1988 | Stupakis .................. | A47C 3/40 248/157 |

FOREIGN PATENT DOCUMENTS

| | | | | |
|---|---|---|---|---|
| DE | 102005052487 A1 | * | 7/2007 | ............. A47C 7/506 |
| DE | 102007022037 B3 | * | 11/2008 | ............. A61G 15/02 |

* cited by examiner

*Primary Examiner* — Milton Nelson, Jr.
(74) *Attorney, Agent, or Firm* — Duncan Palmatier

(57) ABSTRACT

The present invention is a method for performing on-site mobile dentistry utilizing a mobile dental chair and mobile dental lamp in combination. The mobile dental chair can be wheeled to a site and can elevate and recline a patient to a comfortable position for the patient and dentist or dental care provider. The mobile dental chair is driven onto and parked on the flat support base of mobile dental lamp, thereby holding the mobile dental lamp in a safe and stable position. The mobile dental lamp provides high intensity illumination suitable for providing modern dental care. The mobile dental lamp may be provided with removable wheels to aid in transporting the lamp to and from a site.

14 Claims, 5 Drawing Sheets

METHOD AND APPARATUS FOR PERFORMING ON-SITE MOBILE DENTISTRY

FIELD OF THE INVENTION

The present invention relates to a method for performing on-site mobile dentistry utilizing a mobile dental chair and lamp configured to provide an elevated and reclined chair as well as a mobile and stable dental lamp. The disclosed invention allows for on-site dentistry by providing a mobile dental chair that can be wheeled on site, reclined and elevated to place the patient in position for a dentist or dental assistant to perform work, and also by providing a mobile dental lamp that can be wheeled on site and stabilized by placing the mobile dental chair onto part of the lamp's base, thereby holding the lamp in a safe and stable position.

BACKGROUND OF THE INVENTION

Mobile medical care, including dentistry, was once the norm, as practitioners moved from place to place providing their services in "house calls" or even in the street. As dental practices improved and specialized tools were introduced, the model turned to offices, with specialized equipment and staff, where patients were seen by appointment. This office model limited access to dental care to people who could travel to the office and wait to be seen. For many people in need of dental care, this model imposed insurmountable obstacles. In particular, the poor, elderly, workers, and children faced difficulties in traveling to a dental office, waiting to be treated, and taking time from work or school. In 2000, a report by the U.S. Surgeon General called dental disease a "silent epidemic", for which lack of access to care, especially to low income children, was a significant factor. See http://www.nidcr.nih.gov/DataStatistics/SurgeonGeneral/Report/ExecutiveSummary.htm.

In recent years, mobile dentistry has gained popularity. Early applications of mobile modern dentistry focused on efforts to provide dental screening and sometimes preventative care to under served populations by hosting clinics set up in school gyms and community centers. The use of vehicles, such as buses, converted to mobile dental centers, was adopted and this model has predominated the field of mobile dentistry. Such vehicles often include, apart from the vehicle's controls and power train, multiple treatment rooms, a sterilization area, a staff restroom, as well as compressed air systems, power generators, fresh and waste water systems, wheelchair lifts, lighting systems, and heating and air-conditioning systems. These mobile dentistry vehicles seek to replicate a dentist's office and are large, expensive, and require substantial space to locate and time to set up.

Some of the basic problems that mobile dentistry can best solve are not always addressed by these mobile dentist offices. For example, some patients, often elderly patients who cannot move far, if at all, are still not reached. Also, these centers are set up in central locations, but even these may not succeed in reaching many under served populations. For some patients, an on-site visit is the best, or only, means of providing dental care. For such persons, on-site mobile dental services could provide dental care that would otherwise be impossible or very difficult to obtain.

In addition to providing dental care to under served populations, demand has increased for on-site dental services to people traditionally served by dental office visits. Such patients may lack the time, owing to work demands, to travel to a dentist's office and wait to be seen. For such patients, a system of on-site dental services would result in more frequent and efficient dental care.

On-site mobile dentistry is hindered by the specialized equipment needed to hold a patient in a position best suited to the examination of the patient's teeth by the dentist or dental care provider. Dental care can be performed while a patient is sitting in a chair or lying on a bed. This is often the only practical way to provide dental care can be provided to elderly patients who cannot leave a care facility or home. However, a chair or a bed will not hold the patient in a comfortable position for the patient or a good position for the dentist to see and work on the patient's teeth. Chairs and beds are too low for the dentist to perform services without bending over in a highly uncomfortable and stressful position. Performing dental services on a daily basis from an awkward bent position leads to harmful, chronic back pain. In addition, chairs that do not recline and stay in different tilted positions do not hold a patient in a comfortable position to receive dental work, nor is the position conducive to the dentist's performance of dental services. In particular, elderly patients sometimes have trouble swallowing when seated in an upright chair.

In addition to the need for a dental chair, dentistry requires very good lighting, so that the dentist can see the patient's teeth, even the teeth far back in the mouth. Dental offices and large mobile dental vehicles are equipped with specialized dental lamps that can provide proper lighting by which dental work can be performed. Such dental lamps are heavy and often mounted to walls within reach of the dental chair or to a dental chair secured to the floor. For on-site mobile dentistry, conventional home, school, community residence, or other such lighting does not illuminate a patient's teeth adequately, even if the light is directed into a patient's mouth. Small lights, such as dental headlamps, are sometimes used, but these are not capable of providing the lighting a dental lamp can provide. Similarly, light-weight, portable, sometimes battery-powered, LED dental floor lamps are available, but these still fail to provide the illumination of larger dental lamps. In addition, these light-weight lamps stand on flimsy, outwardly extending legs and pose a tripping hazard to the patient and dental staff. Also, these light-weight lamps are prone to falling over, owing to their light weight and unbalanced, relatively top heavy configuration.

Needed is an on-site mobile dental care system that provides a mobile dental chair capable of reclining and elevating a patient into a comfortable position from which a dentist or dental care provider can perform services optimally. Such an on-site mobile dental chair should be easily transportable to various locations, such as a patient's home, residence facility, or community facility, and capable of elevating and reclining a patient into a position from which the dentist or dental care provider can comfortably perform dental services. Also needed is an on-site mobile dentistry system that can provide a mobile dental lamp capable of providing substantial, directed illumination of a patient's teeth. Such an on-site mobile dental lamp should be easily transportable to various locations where dental services will be rendered, and also be stable and not pose a tripping hazard to the patient, dentist, dental care provider, staff, or other persons present.

SUMMARY OF THE INVENTION

The disclosed invention allows for on-site mobile dentistry by providing a mobile dental chair that can be wheeled on site, reclined and elevated to place the patient in position comfortable for the patient and for a dentist or dental assistant to perform work, and also provides an on-site mobile dental lamp that can be wheeled on site and stabilized by placing the mobile dental chair onto part of the lamp's base. The stand is partially stabilized by a base plate of aluminum with a diamond plate gripping surface. The base plate may be round with a diameter large enough to provide substantial support, but small enough so that the person moving the lamp can fit it easily through standard doorways. The lamp's base is thin enough to allow the mobile chair to be moved easily onto and parked on the base surface, and the gripping surface prevents the chair's wheels or the staff from slipping on its surface. By parking the mobile chair on the top surface of the lamp base, the dental light will be in close proximity to the chair and the patient, which helps provide excellent lighting conditions for treating patients. Furthermore, by parking the mobile dental chair on the top surface of the baseplate, exceptional stability for the mobile dental lamp is achieved. The mobile chair may weigh over 250 pounds and the average dental patient weighs about 150 pounds, thereby placing about 400 plus pounds onto the mobile lamp's base, making it stable while in use. The mobile dental chair may have battery power to move it and control the seat's elevation and reclining functions. The mobile dental lamp may have removable wheels to make transportation easier and, when in place, take the wheels out of the way of patients and staff.

DETAILED DESCRIPTION

Figure 5:
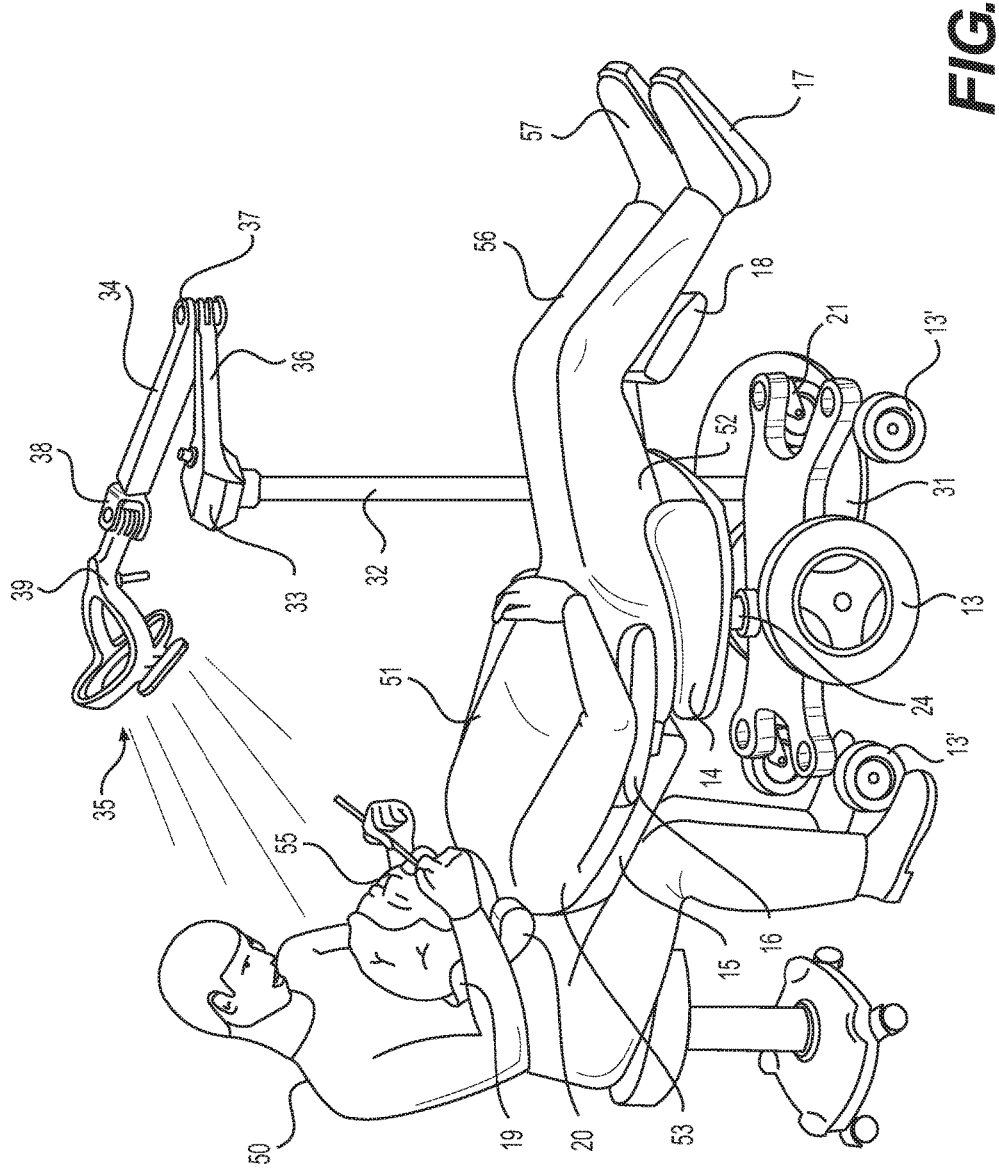
FIG. 5 is a three-quarter perspective view of the mobile dentistry chair and lamp of the present invention in use.

FIG. 5 shows the mobile dentistry chair 11 and lamp 30 set up 10 for a dentist or dental assistant 50 to treat a patient 51. The chair 11 has wheels 13 and 13' to move the chair 11 into an area where dental work will be performed. For example, the mobile chair 11 can be moved into a patient's home, workplace, or location where patients will come for treatment. The chair 11 may be pushed into place or self-propelled by a person sitting in it, or the chair 11 may be powered, such that it can be driven into position. A chair control 27 allows a person sitting in or standing next to the chair 11 to drive it into position, or a remote control (not shown) can operate the chair's 11 powered systems and allow dental staff to drive the chair 11 into position without being seated or standing next to it. The chair control 27 can also manage other powered systems, such as the seat's 14 height, reclining the backrest 15, raising the legrest 18, as described below.

In the preferred embodiment disclosed, the chair 11 has large primary wheels 13 located in the mid-section of the chair's 11 base 12. This arrangement provides substantial support where the majority of the weight of the chair and patient will be exerted. Secondary support wheels 13' provide additional support, especially fore and aft, so that loads exerted, such as when the backrest 15 is lowered and legrest 18 extended, will be supported. The mobile dental chair 11 has a seat 14 with a backrest 15, headrest 19, armrest 16, and legrest 18 with footrests 17. For purposes of dental care, the use of non-absorbent, waterproof and washable upholstery for the seat 14, backrest 15, headrest 19, and legrest 18 is preferred so as to aid sanitation and sterilization.

Figure 1:
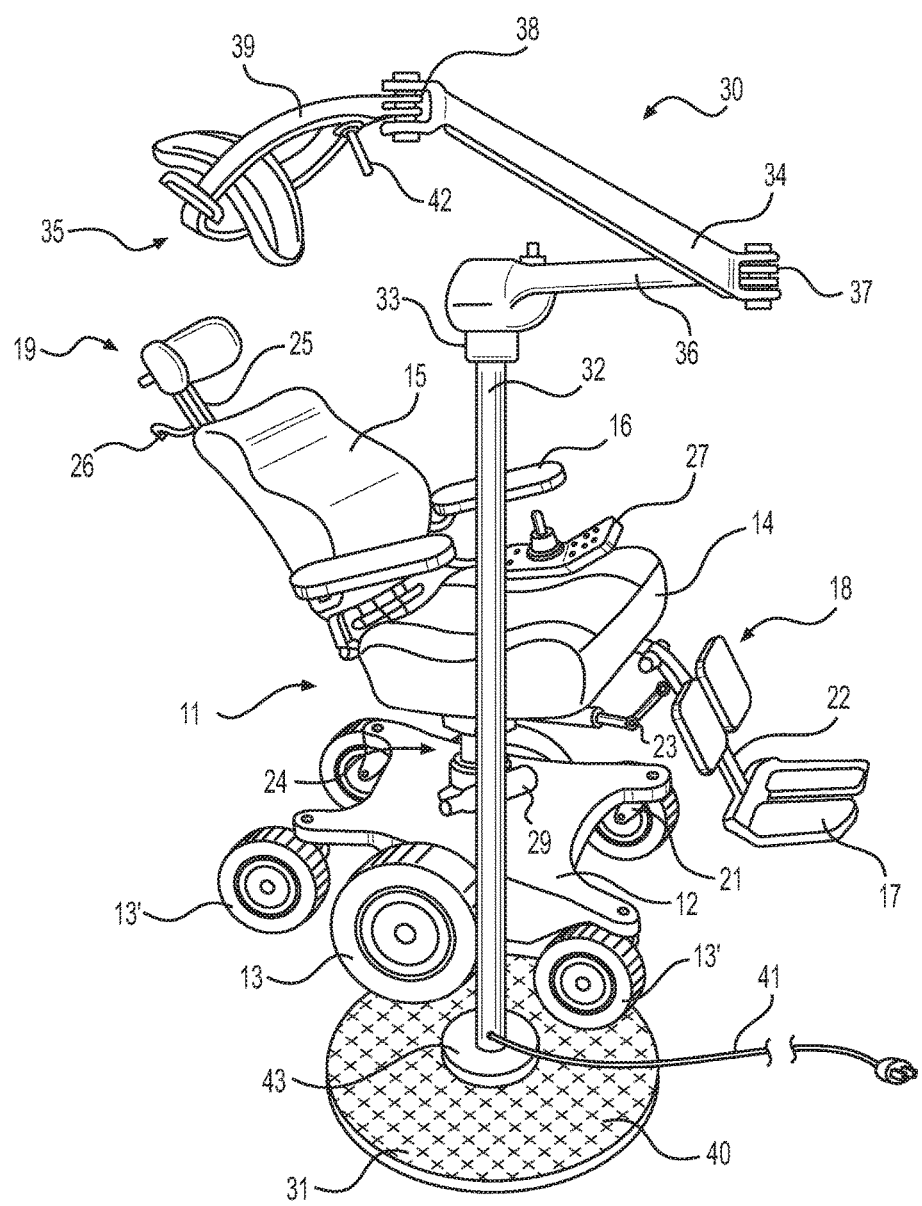
FIG. 1 is a three-quarter perspective view of the mobile dentistry chair and lamp of the present invention.
Figure 2:
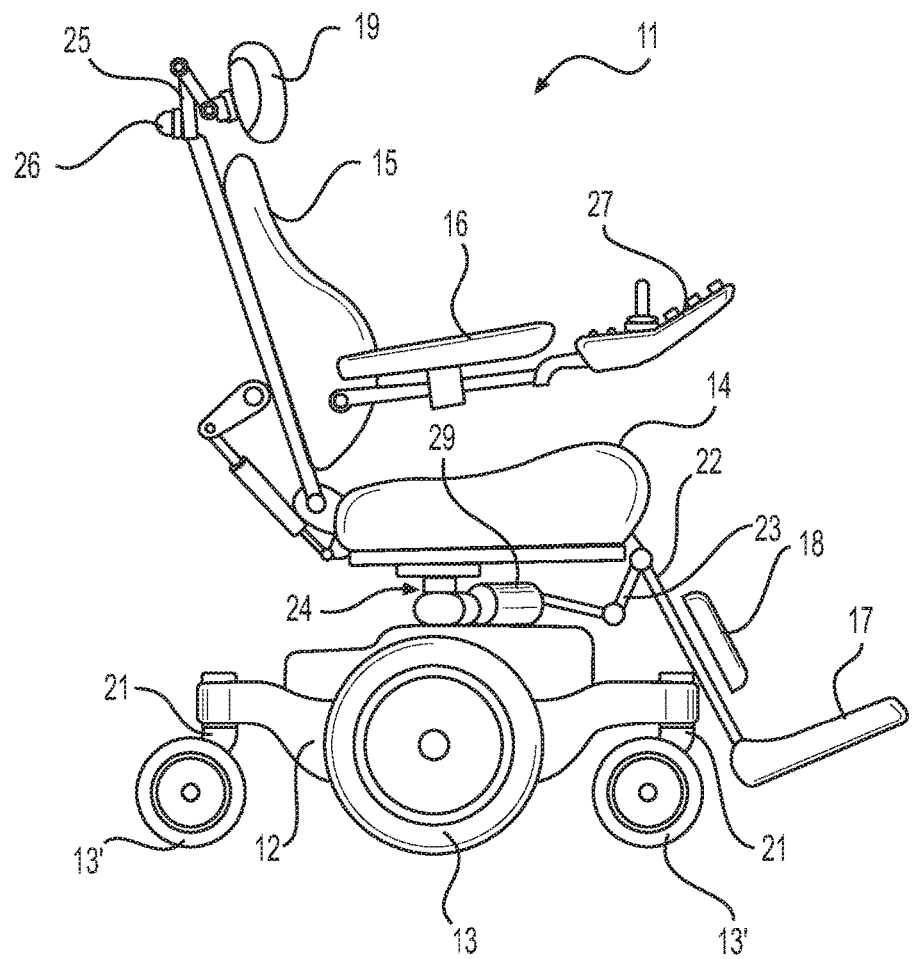
FIG. 2 is a side view of the mobile dentistry chair of the present invention.

As shown in FIG. 5, the backrest 15 has been reclined and legrest 18 extended to place the patient 51 in a near recumbent position, comfortable for the patient and suitable for the dentist 50 to perform work from a convenient and comfortable position. The seat 14 supports a patient's 51 posterior 52. The reclining backrest 15 supports the patient's 51 back 53. Footrests 17 support the patient's 51 feet 57. The headrest 19 supports the patient's 51 head 55. As shown in FIGS. 1 and 2, the headrest 19 is supported on the chair 11 by an adjustable support 25. A headrest adjustment lever 26 can release the headrest 19 so that it can be moved into position and then the lever 26 can operate as a brake to fix the headrest 19 in position. In FIG. 5 a neck rest or pillow 20 has been placed under the patient's 51 neck to provide support, helpful during long procedures, and especially helpful for elderly patients. The legrest 18 supports the patient's 51 legs 56. As shown in FIGS. 1 and 2, the legrest 18 and footrests 17 are secured to the chair 11 by an adjustable leg support chassis 22. A manual adjuster 23 operates as a brake that can be released to allow the leg support chassis 22 to be tilted up and forward, then fixed in that position by tightening the adjuster 23. In the tilted and forward position, the legrest 18 holds the patient's 51 legs 56 during treatment, as shown in FIG. 5. The adjuster 23 can be released to return the legrest 18 to the upright position, as shown in FIG. 1, facilitating exit from the chair 11 and allowing the chair 11, with or without a patient in it, to be transported and wheeled into or out of position.

The chair 11 has a seat 14 mounted to the chassis base 12 by a telescoping elevator 24. The elevator 24 allows the seat to be raised or lowered and held securely in at a selected height. The elevator 24 may be an hydraulic telescope 24, operated manually, such as with a lever (not shown), or powered by an electric hydraulic pump (not shown) to operate an hydraulic telescoping elevator 24 through the chair control 27. Alternatively, the elevator 24 may be a mechanical system, such as a scissor jack (not shown), or a geared system, such as a rack and pinion powered by an electric motor 29. Either mechanical system may be operated manually, such as by a crank (not shown), or electrically powered and controlled by the chair control 27. Whether manual or powered, elevator 24 holds the seat 14 at the desired height. In the case of a powered elevator 24, the hydraulic or electric motor and associated mechanisms (not shown) may operate as a brake to hold the seat 14 at the desired height. In addition, the position of the reclining backrest 15 may be adjusted manually, such as by a lever, or powered with electrical motors through the control 27. Similarly, the legrest 18 may be adjusted as described above or electrically powered and controlled by the chair control 27. Whether manually or electrically operated, leg adjuster 23 or brake holds the legrest 18 in the desired location. In the case of an electrically powered legrest 18, the electric motor and associated mechanism may operate as the brake to hold the legrest 18 in the desired position. For a chair 11 with driven wheels and power-adjusted positions, re-chargeable battery power (not shown) can be incorporated on or within the chassis base 12.

Figure 3:
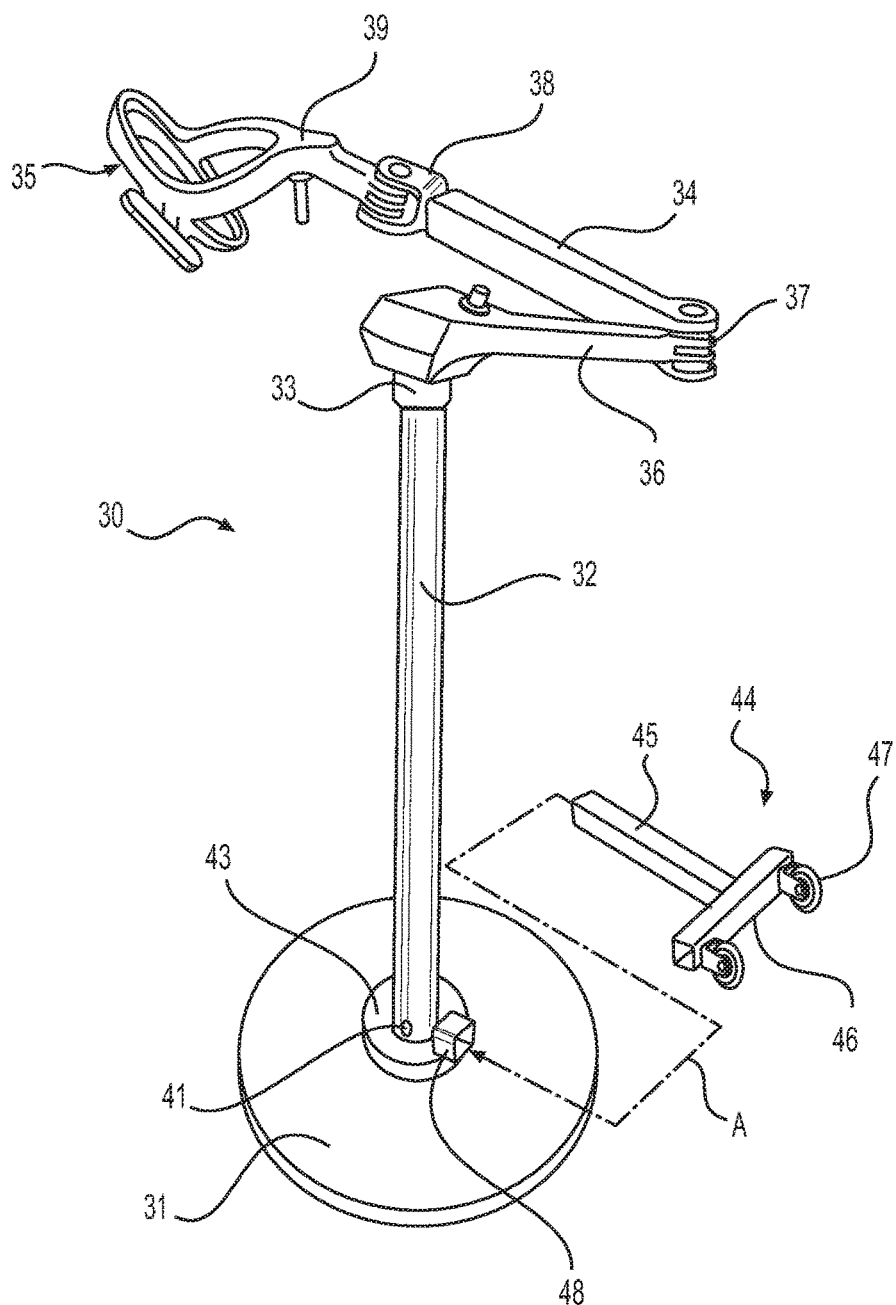
FIG. 3 is a three-quarter view of the mobile dentistry lamp of the present invention.
Figure 4:
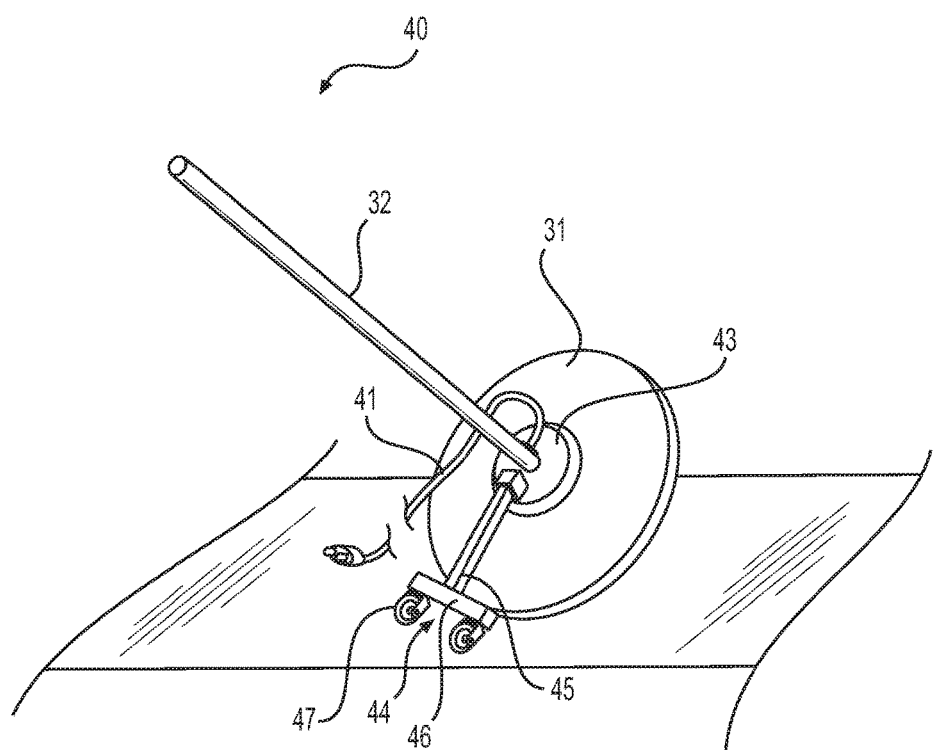
FIG. 4 is a three-quarter perspective view of the mobile dentistry lamp with transport wheels in place.

As shown in FIGS. 1 and 5, the on-site mobile dentistry chair 11 has been moved onto the base 31 of an on-site mobile dentistry lamp 30. In the disclosed embodiment, the lamp base 31 is circular and large enough so that at least two of the chair's 11 wheels, 13 and 13', rest on the lamp base 31. Although the dental lamp's upper mounting 33, swivel arm 34, and light 35 are top heavy, the weight of the mobile chair 11 (about 250 pounds for a battery-powered chair with powered elevation and reclining systems), the patient (about 150 pounds), as well as the lamp's base 31 and counterweight 43 (seen in FIG. 3), securely hold the dental lamp 30 in place even as the heavy dental light 35 is moved to direct light into the area of the patient's 51 mouth being worked on. In a preferred embodiment, the base 31 is formed of ⅛-inch thick plate aluminum and is approximately 29.5 inches in diameter. Aluminum works well for the base plate 31, because it is strong enough to support the dental lamp's upper mounting 33, swivel arm 34, and light 35, yet light enough for easy transport. A base plate 31 thickness of ⅛-inch is thin enough to allow the chair 11 to roll onto and park on the base 31, yet thick enough to provide a stable mounting for the heavy upper mounting 33, swivel arm 34, and light 35 of the dental lamp 30. The base 31 may also include an anti-skid surface 40, such as a diamond pattern formed in the aluminum plate, to prevent the wheels of the mobile chair from slipping the plate's surface and to prevent patients, dental staff, or other persons from slipping on its surface. The diameter of the base 31 may be large enough so that at least two of the mobile dental chair's 11 wheels, 13 and 13', will rest on the plate's surface 31. Also, the 29.5 inch diameter of the base 31 should allow the dentistry lamp 30 to fit easily through standard doorways. The mobile dentistry lamp 30 has a tube 32 to hold the dental light 35 at the correct height for performing work on a patient 51. A tube 32 length of 65 inches has been found to hold the dental light 35 at the right height for lighting a patient's mouth and teeth when the seat 14 of the mobile dental chair 11 is elevated and the backrest 15 is reclined to provide a comfortable position for the patient 51 and dentist 50. Nevertheless, it will be appreciated that the tube 32 may be adjustable to allow the light 35 to be placed at different heights and to make transportation easier. Aluminum tube 32 having a diameter of 2 inches has been found to provide a lightweight and strong support for the heavy upper mounting 33, swivel arm 34, and light 35 of the dental lamp 30. An electrical cord 41 travels from the dental light 35, through the light mount 39, upper swivel 38, upper arm 34, lower swivel 37, lower arm 36, and tube 32, and exits the tube 32 near the base 31. As shown in FIG. 3, the lamp base 31 also includes an iron counterweight 43 to add additional weight at the lamp's 30 base 31, thereby enhancing stability. The tube 32 may be threaded into or welded to the counterweight 43 or base 31. In the preferred embodiment, the mobile dentistry lamp 30 includes a removable transport wheel structure 44 to make transporting the lamp 30 easier. The transport wheel structure 44 has a pair of wheels 47 mounted on each end of a cross piece 46. The cross piece 46 is held on an extension tube 45 that fits into a receiver 48 (indicated in FIG. 3 by direction A) on the counterweight 43. The transport wheels 44 can be placed in the lamp's receiver 48 to allow the lamp 30 to be transported to the location where dental work is performed, then the wheels 44 can be removed so that the dentist 50, dental staff and patient 51 will not trip over it. A releasable pin (not shown) may be used to hold the extension tube 45 in the receiver 48. To transport the lamp 30 from the site, the mobile chair is driven off the base 31, the lamp's power cord 41 is unplugged, the wheels 44 are replaced by sliding the extension tube 45 into the receiver 48, the lamp 30 is tilted so that it is supported by its wheels 47, and the lamp 30 is wheeled out.

The disclosed invention allows for on-site mobile dentistry by providing a mobile dental chair 11 and mobile dental lamp 30 that may be transported in a car or van (not shown) to a site for treating a patient 51, such as the patient's home, school, workplace, or care facility, or to a central location, such as a community center. The mobile dental chair 12 can be removed from the car or van and pushed or driven into the site. Similarly, the mobile dental lamp 30 may be removed from the car or van and wheeled into the site. The mobile dental lamp 30 is placed in position at the site and its transport wheels 44 removed. The mobile dental chair 11 is parked on the lamp's 30 base 31. The lamp's 30 power cord 41 is plugged into a power outlet (not shown) at the site. The patient 51 sits in the chair 11 and the seat 14 is elevated, backrest 15 reclined, and legrest 18 raised to a comfortable position for the patient 51 to receive and for the dentist 50 to perform dental work. The upper mounting 33, swivel arm 34, and light 35 are adjusted with control handle 42 to direct light 35 into the patient's 51 mouth and dental work is performed. After dental services are completed, the upper mounting 33, swivel arm 34, and light 35 are swung out of the way, the seat 14 is lowered, and the backrest 15 and legrest 18 are returned to the sitting position to allow the patient 51 to exit. The mobile dental chair 11 is driven off the base 31 of the mobile dental lamp 30. The power cord 41 is unplugged and the transport wheels 44 secured to the mobile dental lamp 30. The mobile dental chair 11 and lamp 30 can then be removed from the site and returned to the car or van for transportation to the next site.

The drawings and description set forth here represent only some embodiments of the invention. After considering these, skilled persons will understand that there are many ways to perform on-site mobile dentistry with a mobile dentistry chair and lamp according to the principles disclosed. The inventor contemplates that the use of alternative structures, materials, or manufacturing techniques, which result in a method of performing on-site mobile dentistry according to the principles disclosed, will be within the scope of the invention.

I claim:

1. A method of performing on-site mobile dentistry comprising the steps of:

providing a mobile dental chair having a chassis, wheels mounted to the chassis so that the dental chair may move on the wheels, an elevatable seat mounted to the chassis and configured for supporting a human sitting on the seat, wherein the elevatable seat may be elevated and lowered to change a height of the seat, a reclinable backrest configured for supporting a back of the human sitting on the seat, the reclinable backrest having a lower backrest portion and an upper backrest portion distal from the lower backrest portion, wherein the lower backrest portion is adjacent a back portion of the seat and forms a backrest pivot about which the reclinable backrest may be tilted from an upright position to a reclined position and held in a plurality of tilted positions therebetween, a headrest configured for supporting a head of the human sitting on the seat, wherein the headrest is mounted adjustably and adjacent to the upper backrest portion, an extending legrest configured for supporting at least one leg of the human sitting on the seat, wherein the extending legrest has an upper leg portion and a lower leg portion, wherein the upper leg portion of the extending legrest is pivotably mounted adjacent to a forward portion of the seat opposite the back portion of the seat and may be pivoted about the mounting at the forward portion of the seat and held in position from a lowered legrest position configured for the human sitting upright on the seat to a reclined legrest position configured for the human sitting in a reclined position on the seat, and a footrest configured for supporting at least one foot of the human sitting on the seat, wherein the footrest is mounted adjacent the lower leg portion of the legrest, providing a mobile dental lamp having a flat planar support base, a pole extending upwardly from the base, the pole having a lower pole portion mounted to the support base and an upper pole portion distal from the lower pole portion, and a dental lamp mounted to the upper pole portion, transporting the mobile dental lamp to a site where dental services will be performed on a patient, transporting the mobile dental chair by wheeling the mobile dental chair on its wheels to the site, and wheeling the mobile dental chair so that at least one of the wheels of the mobile dental chair rests on the flat planar support base of the dental lamp, having the patient sit in the mobile dental chair, adjusting the elevatable seat, reclining backrest, and extending legrest to support the patient in a comfortable position for the patient to receive dental services from a dental care provider and for the dental care provider to render dental care to the patient, preparing the mobile dental chair for removal from the site following the rendering of dental care by wheeling it off the base of the mobile dental lamp, and removing the mobile dental care lamp and mobile dental chair from the site.

2. The method of providing on-site mobile dentistry of claim 1, wherein the mobile dental chair's wheels are driven by electrical power and operated by a chair control to drive the mobile dental chair to and from the site.

3. The method of providing on-site mobile dentistry of claim 2, wherein the height of the elevatable seat, the reclined position of the reclinable backrest, and the reclined legrest position are adjusted by electrical power.

4. The method of providing on-site mobile dentistry of claim 1, wherein the mobile dental lamp further comprises at least one wheel for transporting the mobile dental lamp to and from the site.

5. The method of providing on-site mobile dentistry of claim 1, wherein the wheel for transporting the mobile dental lamp is removable.

6. The method of providing on-site mobile dentistry of claim 1, wherein the dental lamp mounted to the upper pole portion of the mobile dental lamp further comprises an articulating swivel arm disposed between the upper pole portion and the dental lamp.

7. The method of providing on-site mobile dentistry of claim 1, wherein the flat planar support base further comprises an upper gripping surface to prevent the wheel of the mobile dental chair from slipping.

8. The method of providing on-site mobile dentistry of claim 7, wherein the flat planar support base further comprises a counterweight.

9. In combination, a mobile dental chair and mobile dental lamp for performing on-site mobile dentistry, comprising:

a mobile dental chair comprising a frame, wheels mounted to the frame so that the dental chair may be transported on the wheels to a site where mobile dentistry will be performed, a seat adjustably mounted to the frame, the adjustable seat mounted to the frame by an elevator to raise and lower the height of the seat, the adjustable seat comprising a seat, a reclinable backrest pivotably mounted to the seat to recline the backrest in relation to the seat from an upright position to a reclined position, a backrest recliner brake to hold the reclinable backrest in a reclined position, a headrest mounted to the reclinable backrest, and an extending legrest pivotably mounted to the seat to raise the legrest in relation to the seat from an upright position to the reclined position, and a legrest extender brake to hold the extendable legrest in the reclined position, a mobile dental lamp having a flat support base configured for at least one of the wheels of the mobile dental chair to drive onto and be parked on the support base, wherein the thickness of the support base allows the mobile dental chair to be driven onto and parked on the support base in a position that places the mobile dental chair in a substantially level position relative to a floor on which the mobile dental lamp rests, the mobile dental lamp further comprising a pole secured to the support base and extending from the support base, and a high intensity dental lamp mounted to an opposite end of the pole from the support base.

10. The mobile dental chair and mobile dental lamp combination for performing on-site mobile dentistry of claim 9, further comprising:

a source of electrical power housed by the mobile dental chair and a power control to distribute and control the electrical power, wherein the power control supplies power to drive at least one of the wheels of the mobile dental chair for driving the mobile dental chair to a site at which mobile dentistry services may be provided on site, wherein the power control supplies electrical power to cause the eleva o raise and lower the height of the adjustable seat, wherein the power control supplies electrical power to cause the reclinable backrest to recline to or return from the reclined position, and wherein the power control supplies electrical power to cause the extending legrest to raise to or lower from the upright position.

11. The mobile dental chair and mobile dental lamp combination for performing on-site mobile dentistry of claim 9, wherein the mobile dental lamp further comprises at least one wheel for transporting the mobile dental lamp to and from the site.

12. The mobile dental chair and mobile dental lamp combination for performing on-site mobile dentistry of claim 11, wherein the wheel for transporting the mobile dental lamp is removable.

13. The mobile dental chair and mobile dental lamp combination for performing on-site mobile dentistry of claim 9, wherein the high intensity dental lamp mounted to the opposite end of the pole further comprises an articulating swivel arm disposed between the opposite end of the pole and the high intensity dental lamp.

14. The mobile dental chair and mobile dental lamp combination for performing on-site mobile dentistry of claim 9, wherein the flat support base further comprises an upper non-skid surface.

* * * * *